US00PP18520P3

(12) United States Plant Patent
Recupero et al.

(10) Patent No.: US PP18,520 P3
(45) Date of Patent: Feb. 26, 2008

(54) MANDARIN TREE NAMED 'LATE SEEDLESS MANDARIN'

(50) Latin Name: ***Citrus reticulata* hybrid**
Varietal Denomination: Late Seedless Mandarin

(75) Inventors: Giuseppe Reforgiato Recupero, Acireale (IT); Giuseppe Russo, Acireale (IT); Santo Recupero, Acireale (IT)

(73) Assignee: Future Fruit, LLC, Visalia, CA (US)

( * ) Notice: Subject to any disclaimer, the term of this patent is extended or adjusted under 35 U.S.C. 154(b) by 0 days.

(21) Appl. No.: 11/335,772

(22) Filed: Jan. 18, 2006

(65) Prior Publication Data

US 2007/0169239 P1 Jul. 19, 2007

(51) Int. Cl.
*A01H 5/00* (2006.01)

(52) U.S. Cl. ..... Plt./201

(58) Field of Classification Search ..... Plt./201
See application file for complete search history.

*Primary Examiner*—Kent Bell
*Assistant Examiner*—Annette H Para
(74) *Attorney, Agent, or Firm*—Mark D. Miller

(57) ABSTRACT

A new and distinct seedless mandarin named 'Late Seedless Mandarin' is characterized by late fruit production in April through to late March in the citrus areas of Sicily, Italy and Riverside, Calif. The tree has high yields and bears from year three onwards. It is further characterized by being a triploid and genetically seedless. The seedless fruit is well sized, has a typical mandarin shape (round, flattened) and has acceptable rind thickness with a smooth texture. The fruit has good acid/sugar ratios, has acceptable shipping characteristics, internal and external color is excellent at harvest, and eating quality is excellent. The fruit has an average juice content of about 45% to about 60% at harvest.

13 Drawing Sheets

(*Citrus reticulata* hybrid)

BACKGROUND OF THE NEW VARIETY

The present invention refers to a new late harvesting variety of triploid mandarin which will hereinafter be denominated as the 'Late Seedless Mandarin' tree. The 'Late Seedless Mandarin' tree produces commercially seedless mandarin fruit, bearing in late March through to May in the citrus areas of Sicily, Italy. The 'Late Seedless Mandarin' trees are triploid (three sets of chromosomes). The trees bear from year three and have consistent year-to-year bearing habits. The fruit has acceptable rind thickness, acid-sugar ratios and color, and has an average juice content of 45% to about 60% at harvest.

In the development of new commercial fruit varieties, specific characteristics provide a premium on those fruit varieties that mature late or late in the growing season. For a new fruit variety to be a commercial success the fruit must be of good size, good color, and also have good holding/storage characteristics, advantageous harvest times and shipping characteristics. In addition, the date of maturing must be different from other similar fruit. This new invention meets all of the aforementioned criteria and therefore would be of commercial appeal to the consumer.

The 'Late Seedless Mandarin' variety is a triploid sexual hybrid. Polyploidy in citrus is well known (pgs. 191-193, Spiegel-Roy & Goldschmidt, 1966). Citrus and related genera are typically diploidic and have two sets of 9 chromosomes (2n=18). Triploids, tetraploids and hexaploids exist naturally but occur in low percentages in the population. Citrus triploids are cytologically recognizable by the presence of an additional set of chromosomes. In some cases, triploids are also morphologically recognizable.

ORIGIN AND ASEXUAL REPRODUCTION OF THE NEW VARIETY

The invention (variety) comprises a new and distinct variety of a seedless mandarin plant named 'Late Seedless Mandarin', discovered by the inventors in Azienda Palazzelli Lentini (SR), Sicily, Italy in 1998. The new cultivar is a triploid (3n) selection from sexual crosses made among a tetraploid (pollen bearing) male parent; a 'Avava' Mandarin (4n) (unpatented) and a diploid (seed bearing) female parent ['Fortune' Mandarin (2n) (unpatented)] and referred to as 'Late Seedless Mandarin'. The new cultivar was subsequently asexually reproduced by the inventors in 2000 by in vitro propagation and subsequent bud grafting onto 'Sour Orange' rootstock (200 trees in total). The resulting trees were experimentally evaluated. The resulting tree growth was strong with no bud union abnormalities being noted on the 'Sour Orange' rootstock. An additional 10 trees were asexually reproduced by the inventors in 2004 by bud grafting onto 'Sour Orange' rootstock. An additional 10 trees were asexually reproduced by the inventors in 2004 by bud grafting onto 'Sour Orange' rootstock and grown in Riverside, Calif. The inventors carefully compared all of the asexually reproduced trees with the parent tree, including the fruit, and found, thus far, that they are identical in all respects. The trees under evaluation are free from all known viruses and viroids including Tristeza, Exocortis, Xyloporosis, Stubborn, Citrus Greening disease, Impetratura and Psorosis.

SUMMARY OF THE NEW VARIETY

The 'Late Seedless Mandarin' is particularly characterized by being a triploid, genetically (and hence commercially) seedless, of good fruit size, precocious with stable year-to-year high yields and a late bearing variety (late March to May) in northern hemisphere citrus-bearing regions. The internal fruit quality is excellent.

DETAILED DESCRIPTION

Referring more specifically to the horticultural details of the new and distinct variety of mandarin trees, the following descriptions have been observed under the ecological conditions prevailing at the origin orchard which is located in Sicily, Italy as well as in Riverside, Calif. Color references are to the Dictionary of Color by Maerz and Paul, First Edition, published in 1930. Common colors are also employed.

TREE

Size: Medium, for fourth year tree.
- *Height.*—8 to 10 feet.
- *Width.*—6 to 8 feet at drip line.

Shape: Upright growth habit when grown on 'Sour Orange' rootstock.

Growth: Dense; vigorous branches tend to grow out, upward beyond the trees' general periphery; abundant auxiliary and accessory bud development.

Vigor: Medium.

Productivity: Acceptable for fourth year tree with slight alternate bearing tendencies; fruit produced on the outside and inside of the canopy.

TRUNK

Immediately above the rootstock interface on 'Sour Orange':
- *Size.*—Circumference of 10 to 14 inches, 18 inches above ground.
- *Surface texture.*—Smooth.
- *Color.*—Four year old tree, Andover Green (23-E-2).
- *Lenticels.*—100-200 per sq. cm.

BRANCHES

Size: Scaffold (structural) branches, circumference of 8 to 10 inches. Secondary Branches (on which fruit bearing branches are borne) circumference of 3 to 5 inches.

Angle of branches: Average between about 30° and about 40°.

Color of branches over two years old: Andover Green (23-E-2).

Color of branches less than two years old: Brunswick Green LT$^{P}$ (22-L-10).

Figure 1A:
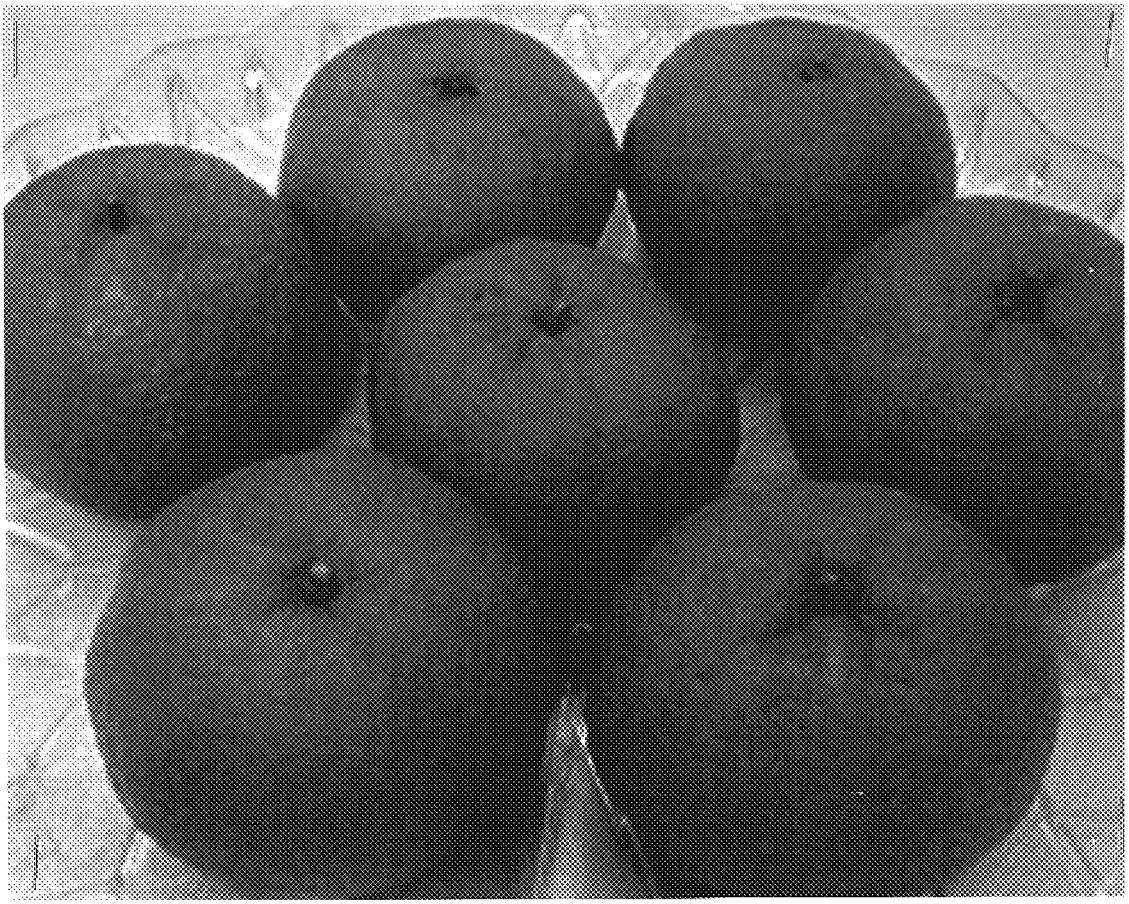
FIGS. 1A, 1B and 1C are color photographs providing an overall perspective view of several specimens of typical whole fruit.
Figure 1B:
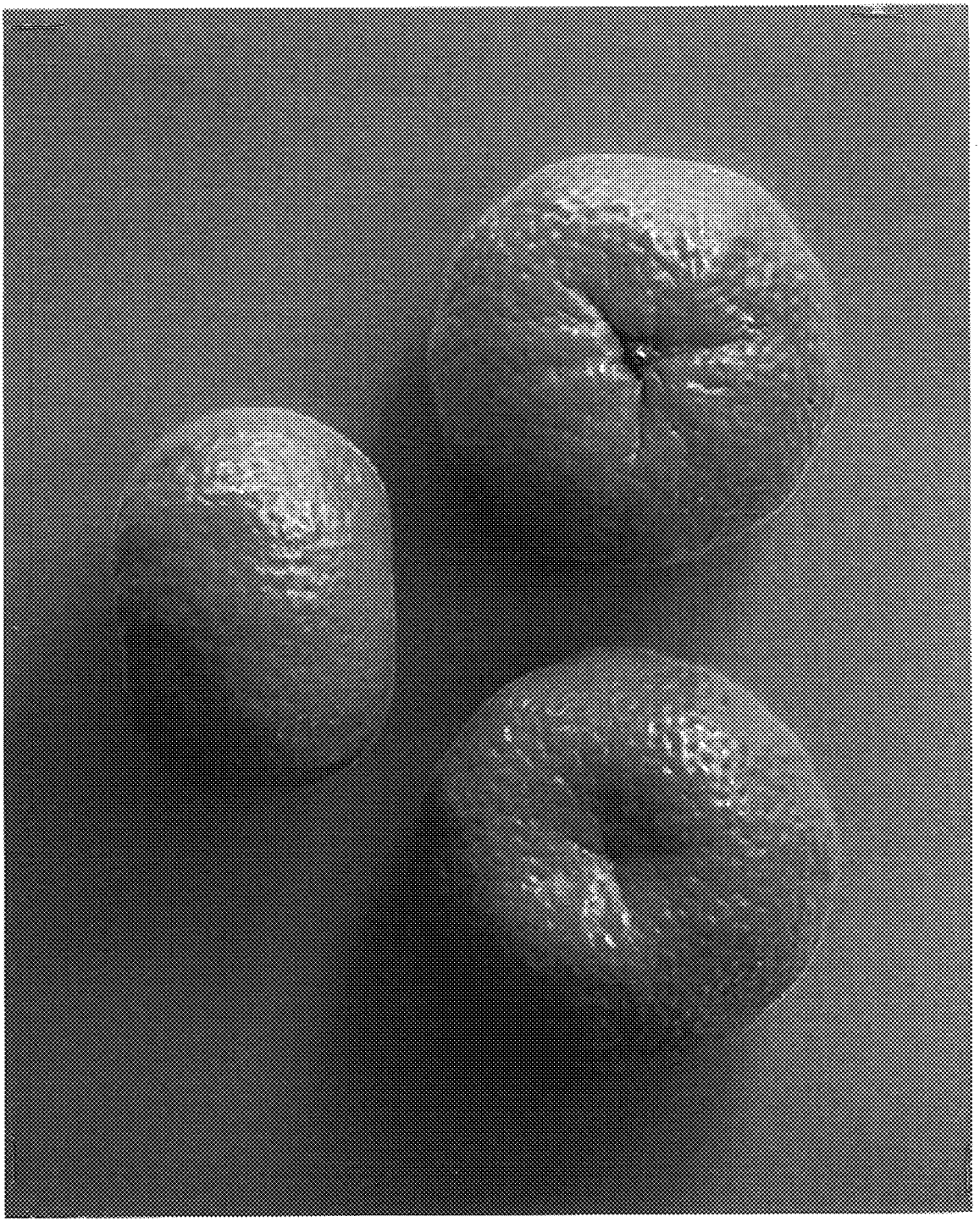
Figure 1C:
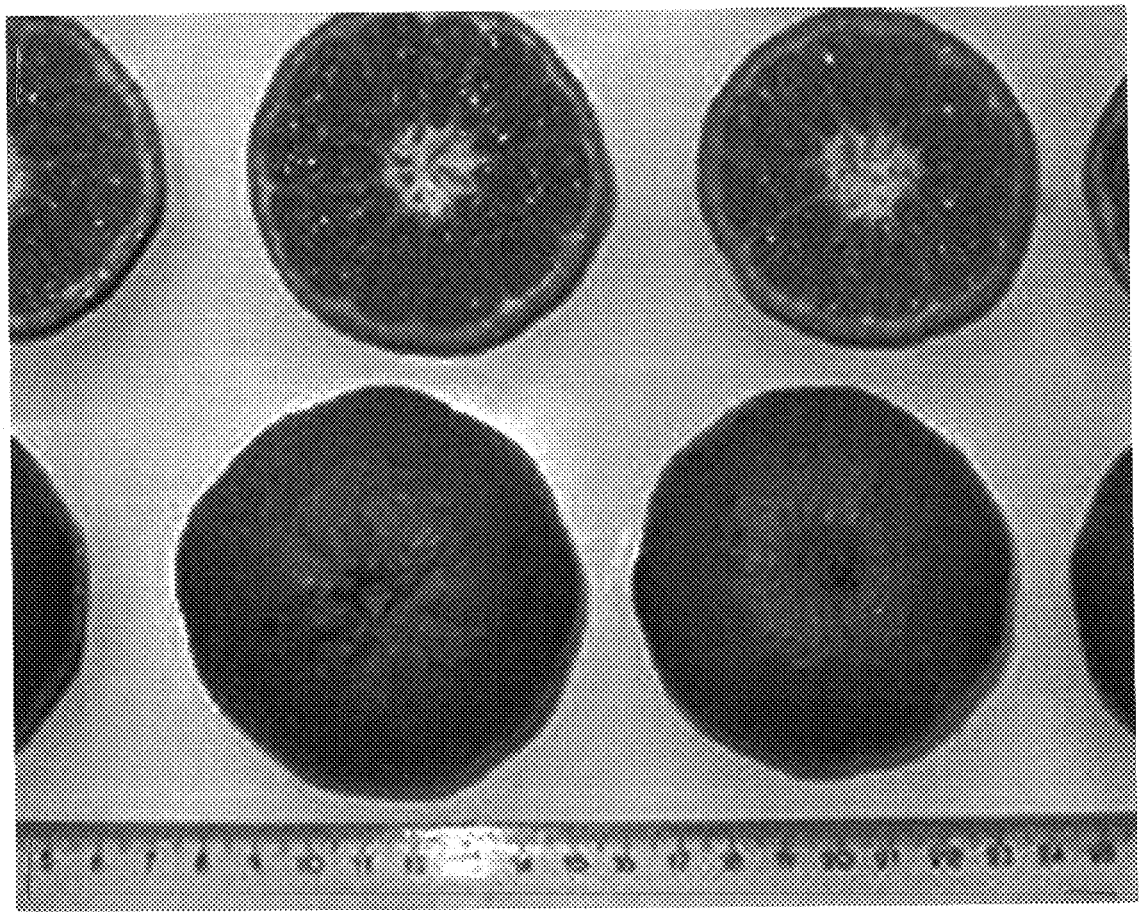
Figure 2:
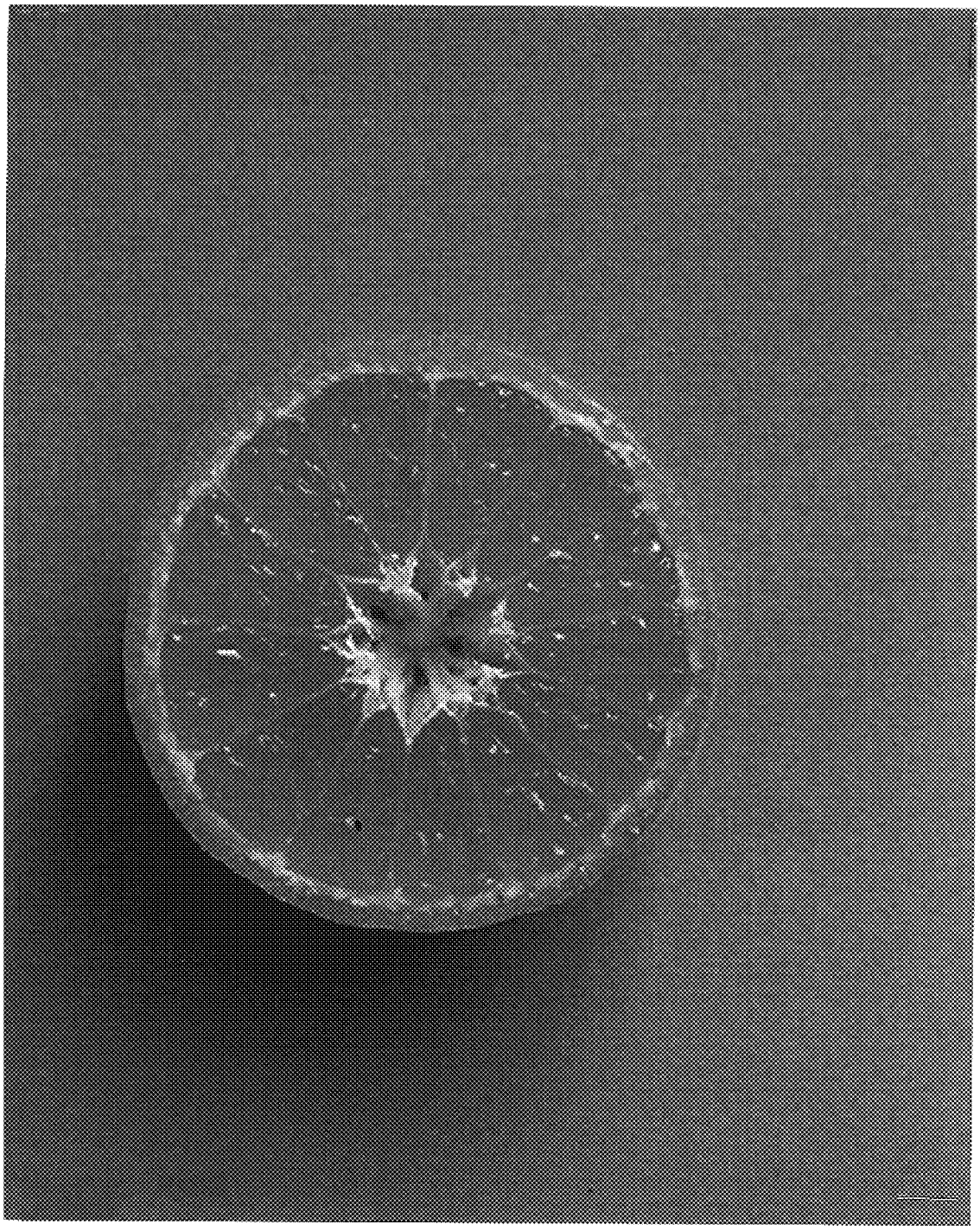
FIG. 2 is a color photograph illustrating a transversely cut fruit of the present invention harvested in January 2004.
Figure 3:
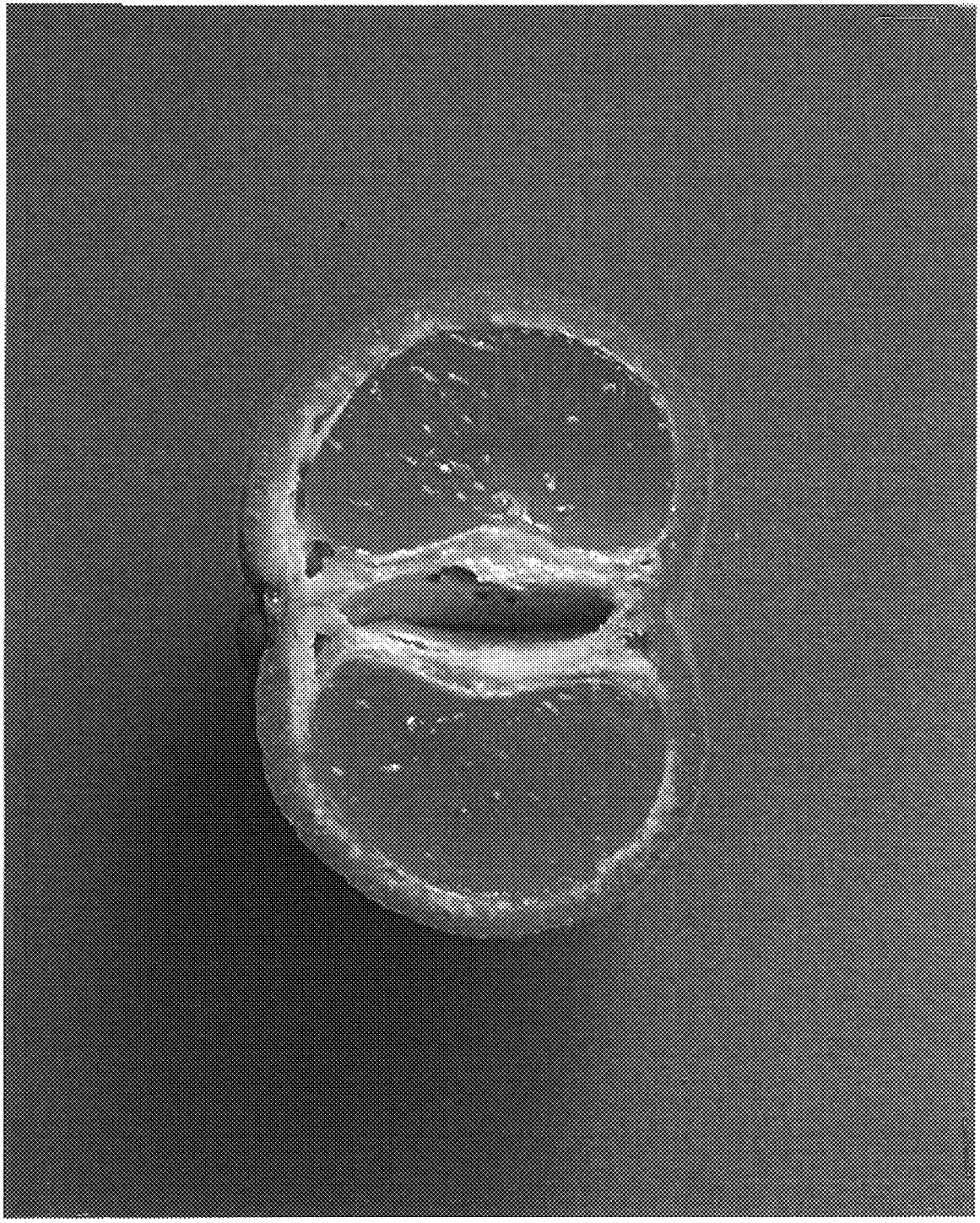
FIG. 3 is a color photograph illustrating a typical view of a longitudinally cut fruit of the present invention harvested in January 2004.
Figure 4:
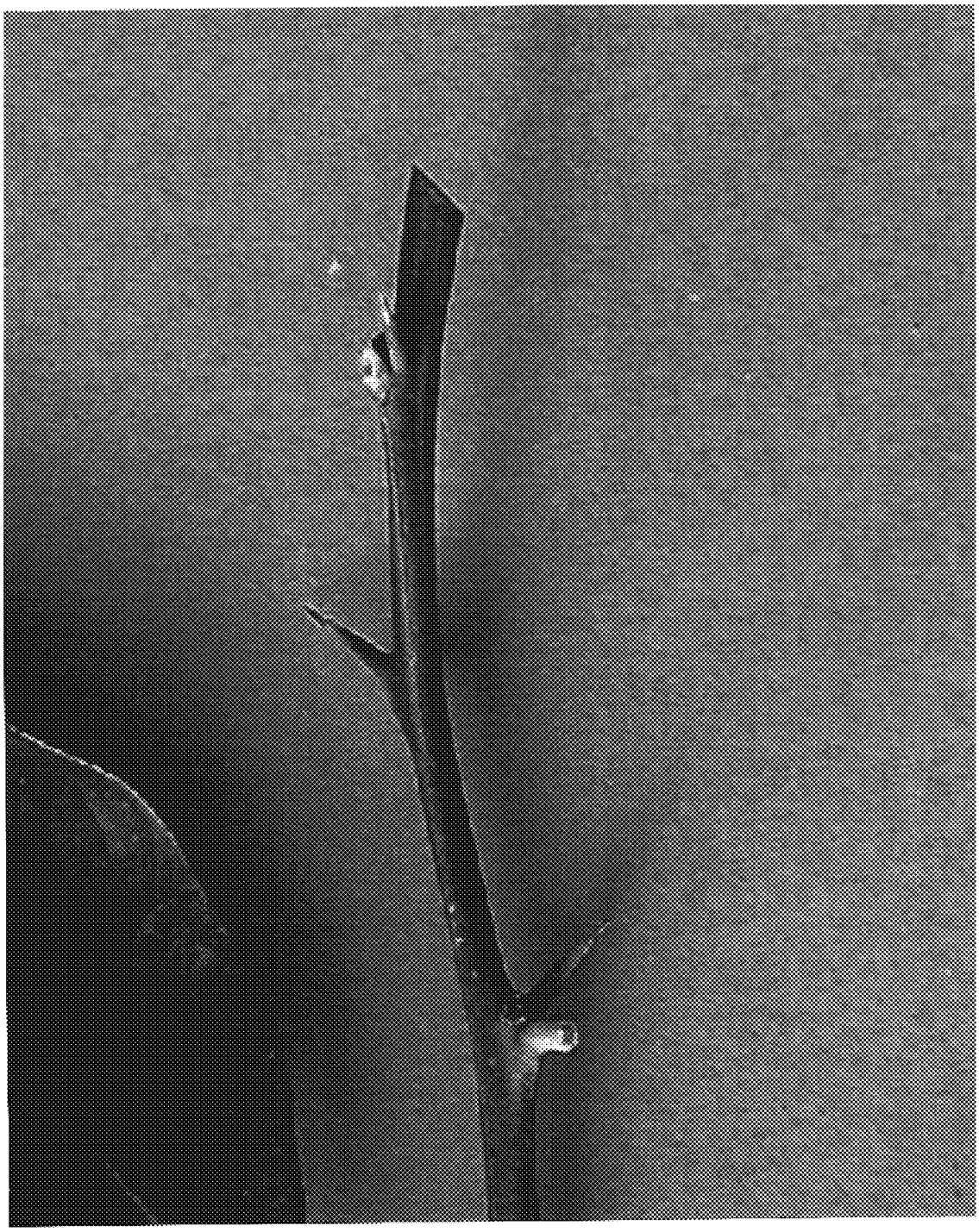
FIG. 4 is a color photograph of a typical thorn produced on a one year old branch of the present invention which becomes reduced in subsequent years.

Thorns: Many on young branches (FIG. 4) becomes less prominent on older branches (FIGS. 5A and 5B).
- *Length.*—10 to 15 mm (0.39 to 0.59 in.).
- *Width.*—2 to 3 mm at base (0.08 to 0.12 in.).

LEAVES

Figure 5A:
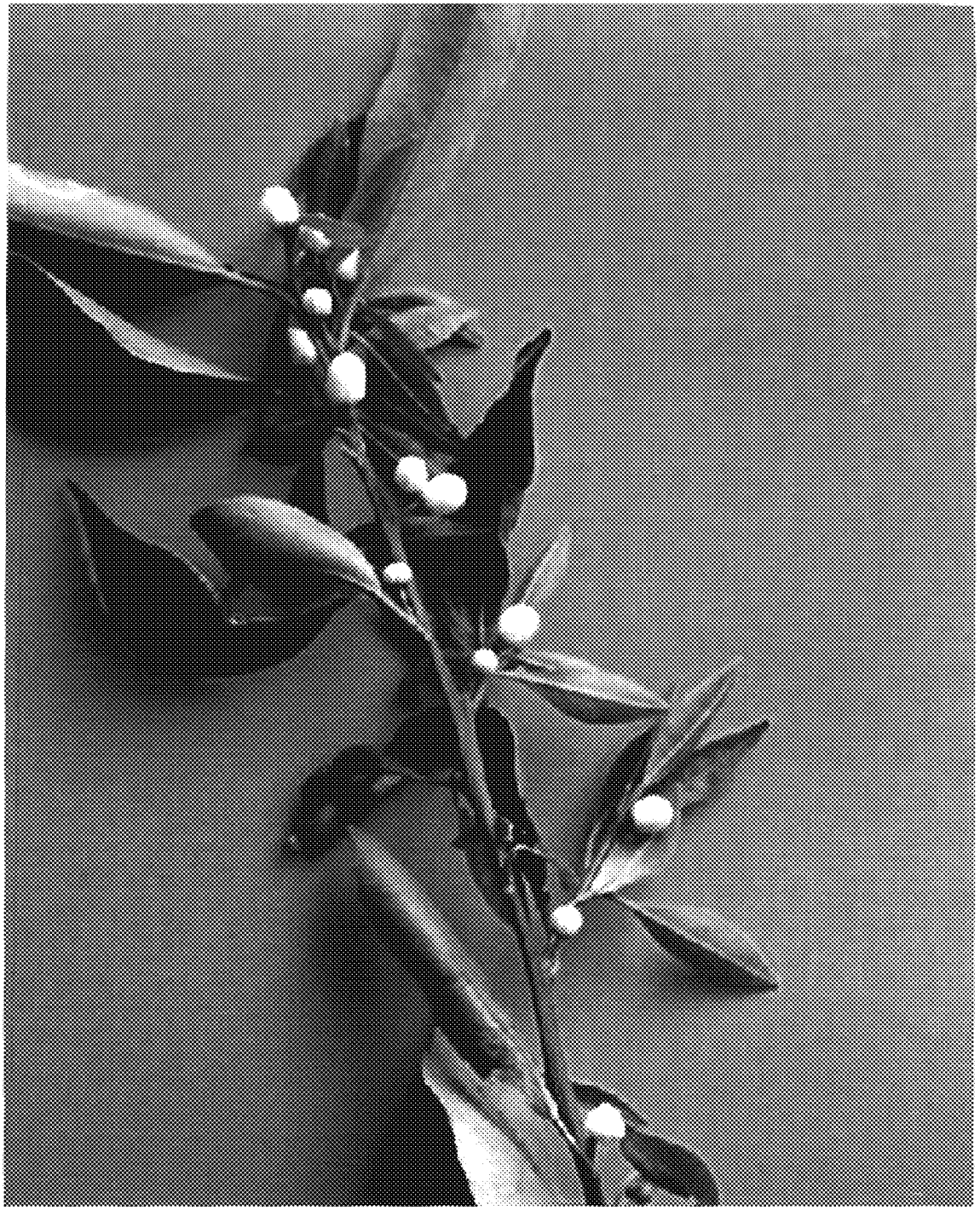
FIGS. 5A and 5B are color photographs illustrating a typical view of the leaf and flower arrangement on a two year old branch of the present invention. The branch is basically thornless.
Figure 5B:
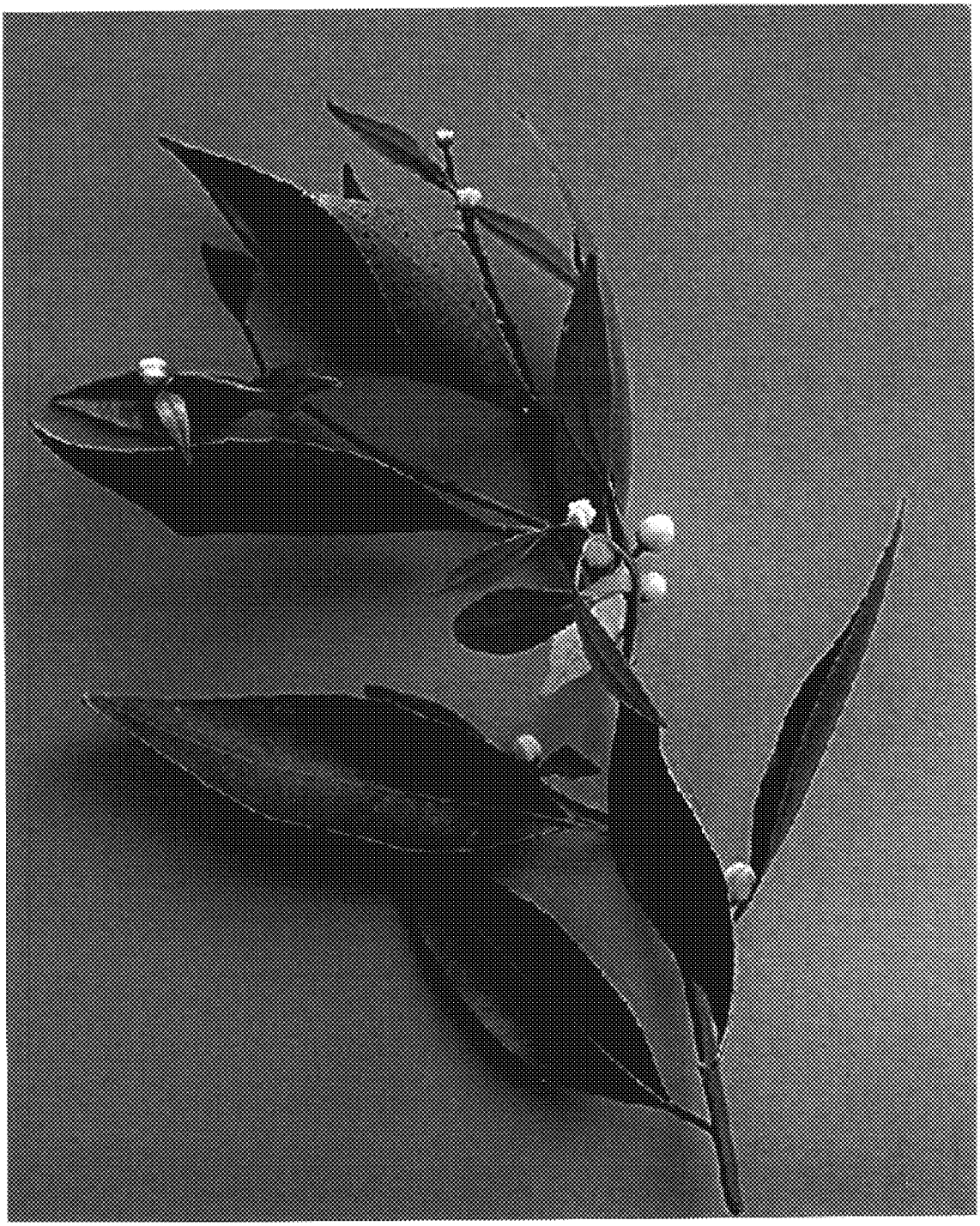
Figure 6:
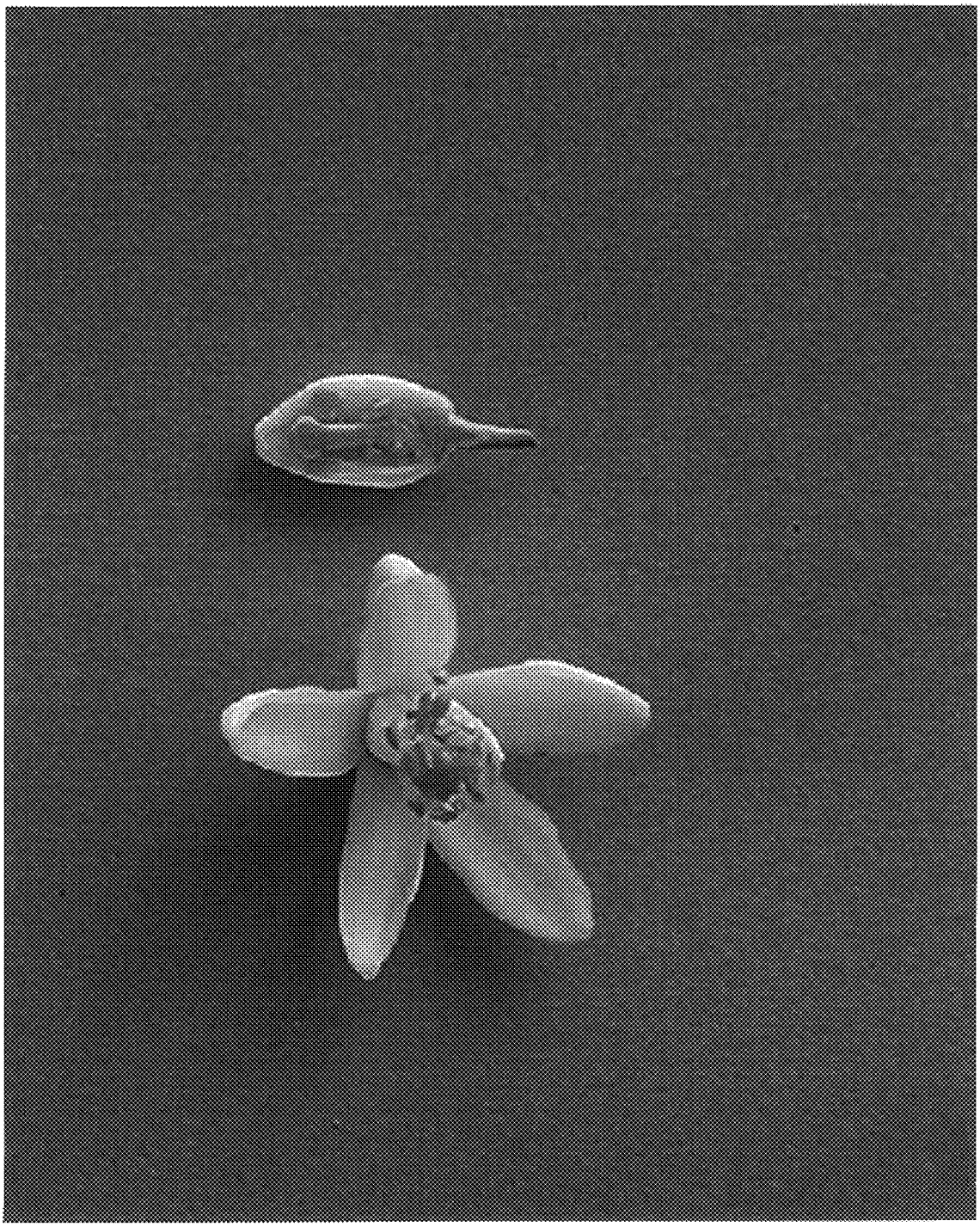
FIG. 6 is a color photograph of a longitudinally cut flower as well as a top view of a flower of the present invention.
Figure 7:
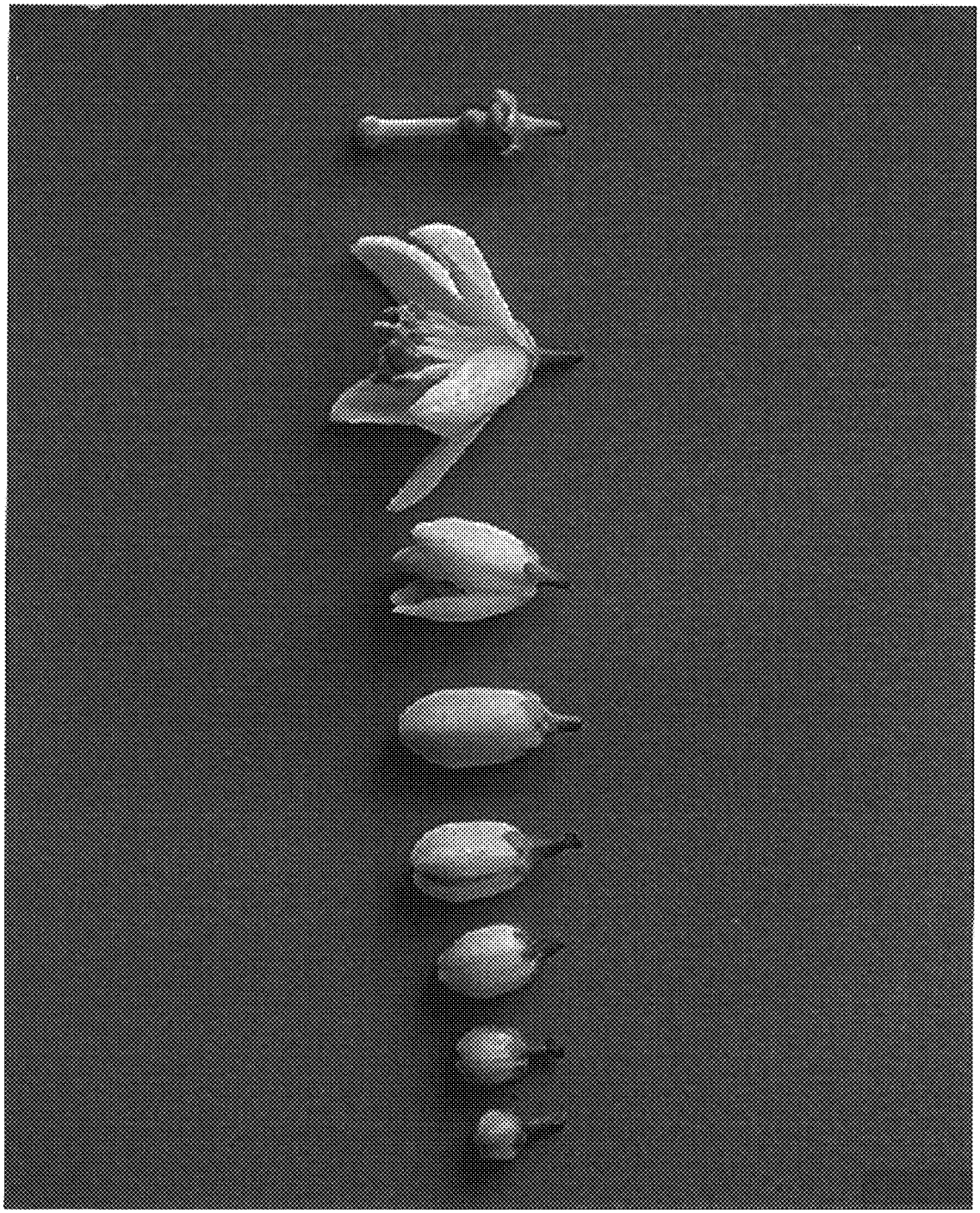
FIG. 7 is a color photograph of the typical flower development from white bud stage to fruitlet stage of the present invention.
Figure 8:
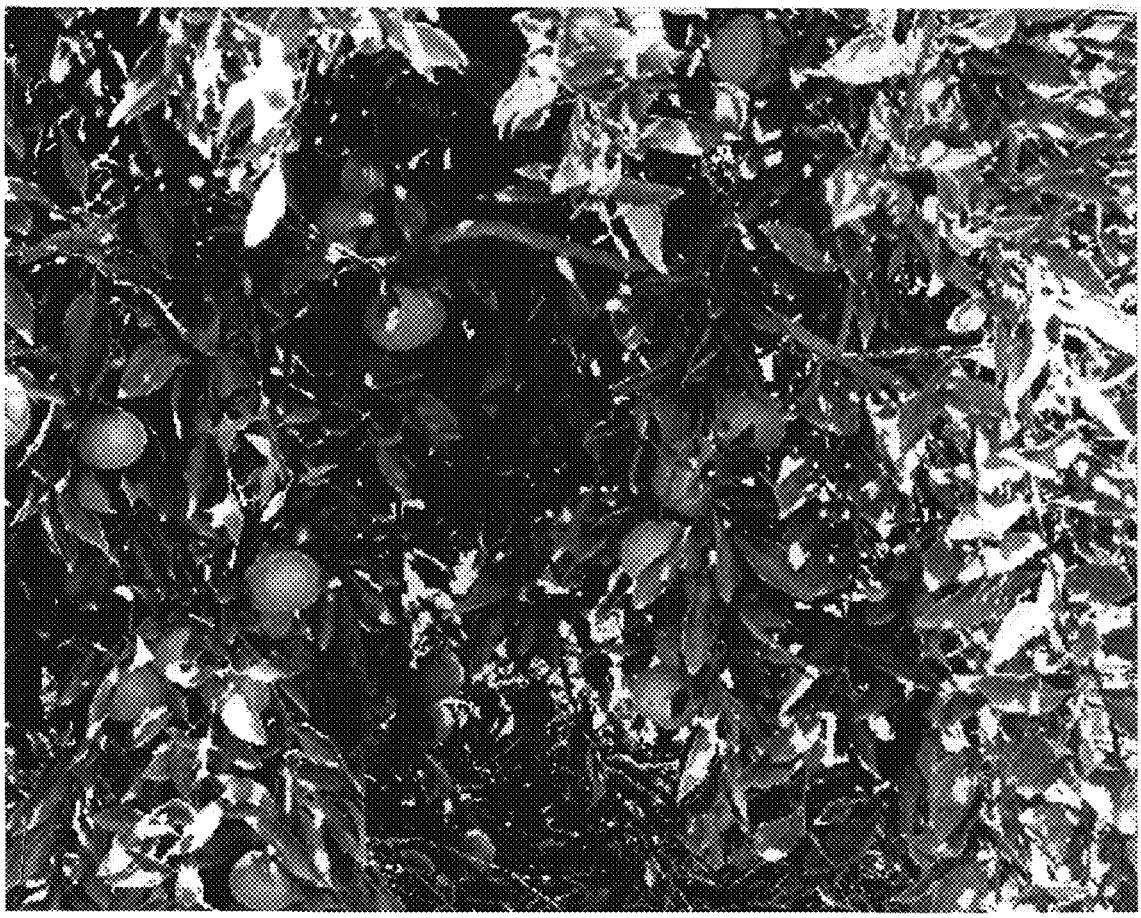
FIG. 8 is a color photograph of typical fruit production of a four year old tree of the present invention.
Figure 9:
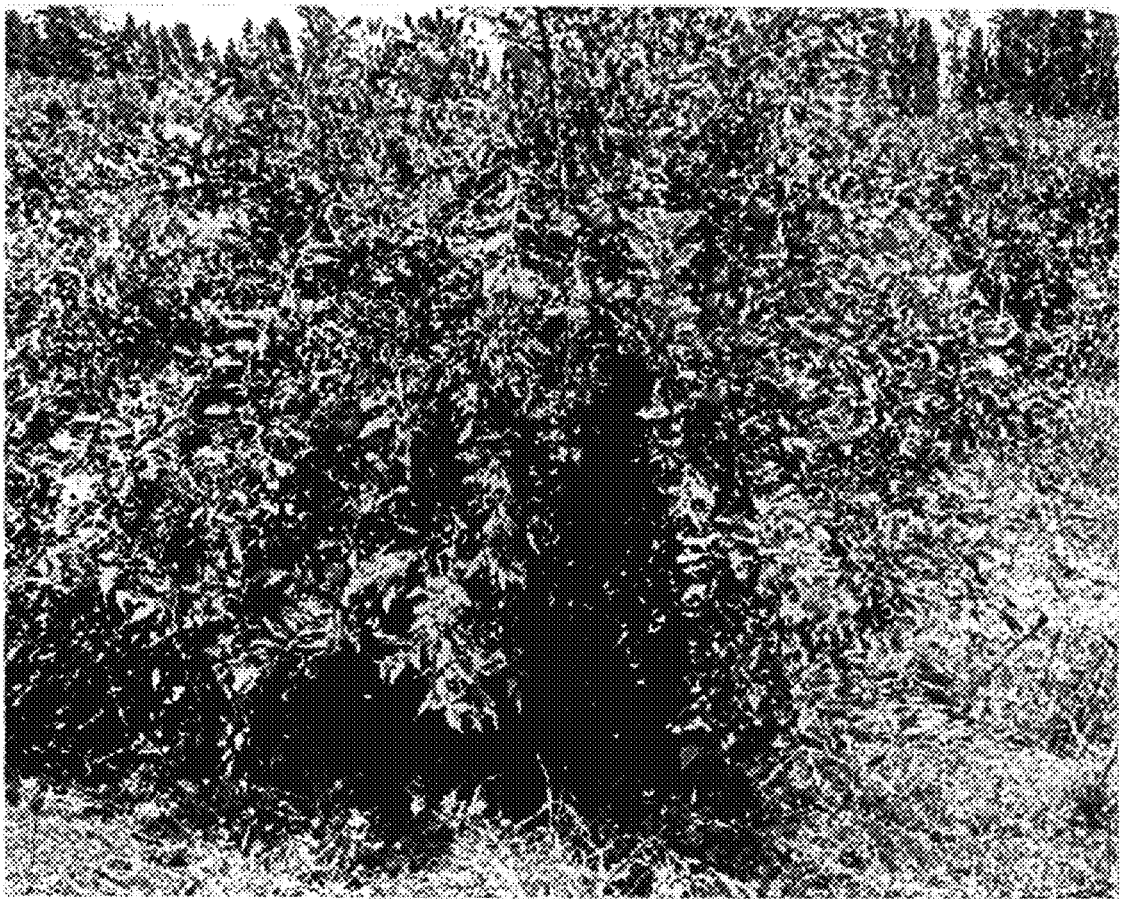
FIG. 9 is a color photograph of an overall view of a four year old tree at the onset of harvest showing fully colored fruit of the present invention.

The leaves are alternate, unifoliate with distinct articulation between the petiole and leaf blade. They exhibit a slight curvate morphology along the longitudinal axis without significant undulation and have minimal basal wings (FIGS. 5A and 5B).

Size: Medium.
- *Length.*—75 to 125 mm (3 to 5 in.).
- *Width.*—38 to 76 mm (1.5 to 3 in.).

Texture: Smooth, lacking depressions in the adaxial surface. Abaxial surface has raised leaf veins.

Shape: Elliptically oval to oblong. Acute tips.

Margin: Mild serrations at edge.

Apex: Minor crenation on acute leaf tip.

Base: Slightly elongated.

Edges: Distinctly smoother towards the basal leaf end.

Marginal oil cells: Many, 8 to 10 per linear cm; cells are ovoid and smooth.

Color: Mature leaves are glossy.
- *Upper surface.*—Alfalfa Green+ (22-C-12).
- *Lower surface.*—Piquant Green (20-K-6).
- *Petioles.*—Reduced, not prominent wings (FIGS. 5A and 5B).
- *Length.*—Less than 8 to 15 mm (0.33 to 0.6 in.).
- *Diameter.*—Approximately 2 to 4 mm (0.08 to 0.16 in.).
- *Color.*—Alfalfa Green+ (22-C-12).

Venation: Distinct, pinnately reticulated.
- *Midvein.*—Width: At base, 1 to 2 mm (0.04 to 0.08 in.); at apex 0.3 to 0.4 mm (0.01 to 0.16 in.).
- *Color.*—Chrome Green+ (22-L-12).

FLOWERS

The flowers are small, terminal and complete. Flower buds have little or no anthocyanin coloration during development. Flowers are borne in single or multiple clusters. Anther color is pale yellow to yellow. Pollen fertility is very low to sterile as indicated by the observation that less than 0.01% of the pollen grains stained with acetocarmine. The flowers have a sweet, pleasing citrus fragrance.

Flower buds:
- *Shape.*—Ten days prior to anthesis, slightly ovoid, 10 mm (0.4 in.) in diameter. One to two days prior to flowering, elongated cone, 6 to 10 mm (0.24 to 0.4 in.) in diameter.

*Length.*—12 to 20 mm (0.48 to 0.8 in.)
*Calyx.*—4 to 5 sepals, fused forming a cup-like calyx.
*Color.*—Calliste Green (19-L-6).
*Lobe tips.*—Blunt but with apiculate tips.

Date of normal first bloom:
*Sicily, Italy.*—First bloom about March 15$^{th}$; end bloom about April 15$^{th}$.
*Riverside, Calif.*—First bloom about April 1$^{st}$; end bloom about April 20$^{th}$.

Flowers: Medium, in clusters of three to five.
*Diameter.*—When fully opened, 20 to 25 mm (0.8 to 1.0 in.).
*Bloom quantity.*—Abundant (typical of a Mandarin) non-alternate bearing.
*Petals.*—4 to 5, rounded to acute tips. Size: Small (compared to other citrus species). Length: 10 to 15 mm (0.4 to 0.6 in.). Width: 4 to 7 mm (o.15 to 0.3 in.). Form: Narrow, linear, slightly oblong. Color: Adaxial surface: White (1-A-1). Abaxial surface: White (1-A-1). Claws: None. Petal Margins: Smooth, slightly pointed to slightly rounded at tips.
*Pedicel.*—3 to 5 mm (0.12 to 0.2 in.) average. Color: Sea Green (19-K-6).
*Sepals.*—Number: 15 to 20, with complete style development. Length: 10 to 15 mm (0.4 to 0.6 in.). Filament color: White (10-A-1). Anthers: Length: 2 to 4 mm (0.08 to 0.12 in.). Width: 1 to 2 mm (0.04 to 0.08 in.).
*Stamen.*—Number: 15 to 20, with complete style development. Length: 10 to 15 mm (0.4 to 0.6 in.). Filament color: White (10-A-1). Anthers: Length: 2 to 4 mm (0.08 to 0.12 in.). Width: 1 to 2 mm (0.04 to 0.08 in.). Color: Aureolin$^{P}$ (10-L-2).
*Pistil.*—Stigma: Ovoid shape, 2.5 to 3 mm (0.1 to 0.12 in.) in diameter. Color: Pineapple (11-J-2). Style: Length: 6 to 10 mm (0.24 to 0.4 in.). Width: 2 to 3 mm (0.08 to 0.12 in.). Ovary: Ovoid shape, 6 to 8 mm (0.24 to 0.32 in.) in diameter. Color: Imperial Jade (21-L-12).

FRUIT

On grafted trees the first fruit production occurred after three seasons. The fruit flesh has an intense uniform color (FIGS. 1A to 1C, 2 and 3). The fruit is seedless. There is no persistence of the style on the fruit.

Internal characteristics:
*Flesh color.*—Bitter Sweet Orange (3-B-12).
*Interior segments.*—Average of 9 to 13 in number.
*Interior segment membranes.*—Thin.
*Pulp vesicles.*—Medium. Length: 6 to 8 mm (0.24 to 0.32 in.). Diameter: 2 mm (0.08 in.). Color: Bitter Sweet Orange (3-B-12).
*Septa.*—Dorsal slightly convex contoured character. Slight separation in the middle.
*Juice.*—Abundant in mature fruit, evenly distributed in sections. Typical mandarin flavor, rich with low acid and high sugar (10 to 13 BRIX at harvest, sugar/acid ratio at harvest over 8), well blended (pH is 3.3 to 3.8).
*Fruit center.*—Exhibits separation, with a diameter of approximately 8 to 12 mm (0.32 to 0.48 in).

External characteristics:
*Rind oil cells.*—Medium to large, and occur at a density of approximately 150 to 200 per cm$^2$.
*Glandular layer.*—2 to 3 mm (0.08 to 0.12 in.).
*Mesocarp (albedo).*—2 to 3 mm (0.08 to 0.12 in.).
*Axis.*—Separated, 3 to 5 mm (0.12 to 0.2 in.) in diameter.

Fruit weight: Average of 140 g to 160 g (4.9 oz. to 5.6 oz.) (mean of 100 fruit per tree and 5 trees).

Date of maturity:
*Sicily, Italy.*—About March 15$^{th}$ to the middle of May.
*Riverside, Calif.*—About the end of March to the middle of May.

Size: Medium.
*Length.*—50 to 64 mm (2 to 2.5 in.).
*Width.*—50 to 89 mm (2.0 to 3.5 in.).

Form: Round and flattened (typical mandarin shape, FIGS. 1A and 1B).
*Basal stem end.*—Slightly depressed.
*Base.*—Diameter 20 to 25 mm (0.8 to 1.0 in.).
*Stem.*—Length 10 to 25 mm (0.4 to 1.0 in.).
*Calyx.*—Diameter 6 to 10 mm (0.24 to 0.4 in.).
*Apex.*—Slightly raised shoulders, depressed center.
*Stylar scar.*—None.

Figure 10:
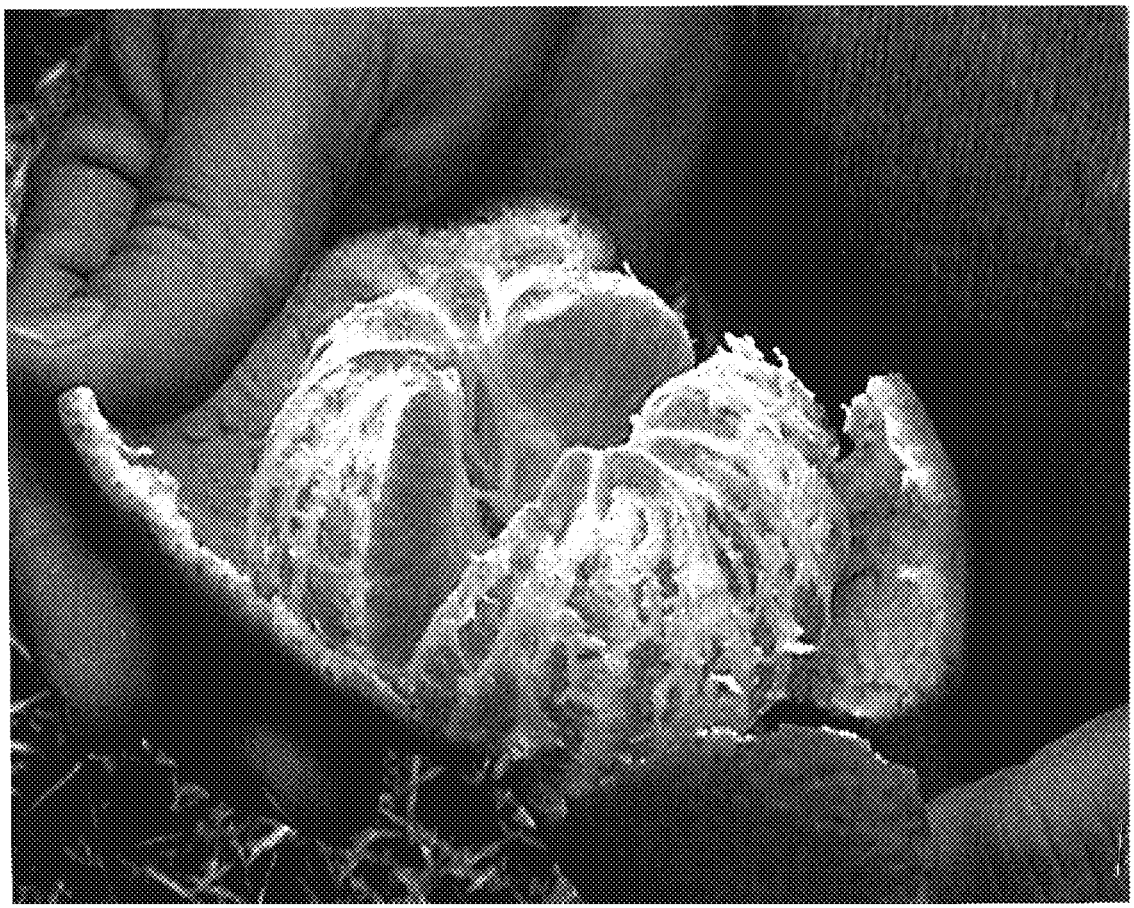
FIG. 10 is a color photograph of a partially peeled fruit showing the easy skin removal and segment separation.

Rind:
*Surface.*—Smooth, easy peelability and internal segment separation (FIG. 10).
*Thickness.*—Average, 3 to 6 mm (0.12 to 0.24 in.).
*Color.*—Mandarin (2-E-12) at first harvest (March).

Use: Fresh market or juice or processing.

Keeping quality: Similar to late mandarins.

Post harvest disorders: Similar to existing mandarin varieties.

The above description of this new variety of mandarin is based on the growing conditions prevalent in Sicily, Italy and in Riverside, Calif. Variations of the usual magnitude, such as differences in maturity date and production, may be due to cultural practices, including irrigation, fertilization, pruning, fruit thinning and primary climate changes as well as soil conditions.

Table 1 below compares the fruit skin color, seeds and pollen fertility between fruit harvested from the 'Late Seedless Mandarin' as compared to the Clementine variety, 'Fortune' Mandarin.

TABLE 1

| Tree | Fruit Skin Color (Apr. 15, 2002) | Seeds/fruit* (Apr. 15, 2002) | Pollen Fertility** |
|---|---|---|---|
| 'Fortune' Mandarin | Mandarin (2-E-12) | 10 to 25 | 90% |
| 'Late Seedless Mandarin' | Mandarin (2-E-12) | 0 | <0.01% |

*500 fruit assessed per tree, 5 trees.
**Estimated by acetocarmine staining during flowering in April.

Table 2 details some preliminary yield data for 'Late Seedless Mandarin' tree grafted onto 'Sour Orange' trees.

TABLE 2

| | Typical Yield | |
|---|---|---|
| Year | Yield | Average Fruit Size |
| Yr. 1 | 0 | |
| Yr. 2 | 5 kg (11.05 lb.) | 179 g (6.265 oz.) |
| Yr. 3 | 25 kg (55.25 lb.) | 181 g (6.335 oz.) |
| Yr. 4 | 78 kg (172.38 lb.) | 155 g (5.425 oz.) |

Table 3 details some fruit comparisons between 'Fortune' Mandarin and 'Late Seedless Mandarin' fruit harvested on Apr. 15, 2002.

TABLE 3

| Variety | Juice % | BRIX | Acid % | Fruit Diameter | External Color Intensity* | Pulp Odor Intensity** | Pulp Color*** |
|---|---|---|---|---|---|---|---|
| 'Late Seedless Mandarin' | 58.6 | 11.47 | 1.7 | 7.56 cm | 4.56 | 6.69 | 6.56 |
| 'Fortune' Mandarin | 42.0 | 13.63 | 0.75 | 4.19 cm | 7.69 | 5.25 | 5.31 |

Assessed on a scale of 0 to 10 as follows:
*External Color: 0 = Completely green, Calliste Green (19-L-6); 10 = Fully orange, Mandarin (2-E-12).
**Pulp Odor: 0 = No detectable odor by human testing panel; 10 = Rich citrus odor, typical of a fully matured mandarin such as 'Fortune' Mandarin when fully mature from late March to May.
***Pulp Color: 0 = The onset of color development during the beginning of juice sac fill; 10 = Full maturity pulp color typical of a fully matured mandarin such as 'Fortune' Mandarin when fully mature from late March to May.

TABLE 4

Typical Picking Pattern of the 'Late Seedless Mandarin' tree in Sicily, Italy

| | | |
|---|---|---|
| First Pick | 25% of total | Late March |
| Second Pick | 25% of total | Mid April |
| Third Pick | 50% of total | Mid May |

20% of the fruit will be below the first grade quality criteria.

What is claimed is:

1. A new and distinct variety of a seedless mandarin tree as described and illustrated called 'Late Seedless Mandarin' that is characterized as a triploid having late fruit production from about late March through to about mid May in the citrus areas of Sicily, Italy and Riverside, Calif., the trees coming into bearing by year 3 with seedless fruit having a typically mandarin flattened round shape, an average juice content at harvest of about 45% to about 60% with smooth skin texture, and having acceptable rind thickness, acid-sugar ratios, color and pulp eating quality.

* * * * *